US00PP34850P2

(12) United States Plant Patent
Clark et al.

(10) Patent No.: US PP34,850 P2
(45) Date of Patent: Dec. 20, 2022

(54) GRAPE PLANT NAMED 'INDULGENCE'

(50) Latin Name: ***Vitis* L. hybrid**
Varietal Denomination: Indulgence

(71) Applicant: THE BOARD OF TRUSTEES OF THE UNIVERSITY OF ARKANSAS, Little Rock, AR (US)

(72) Inventors: John R. Clark, Fayetteville, AR (US); Renee T. Threlfall, Springdale, AR (US); James N. Moore, Arlington, TX (US); Justin R. Morris, Springdale, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/532,216

(22) Filed: Nov. 22, 2021

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 206, 207
CPC ..... A01H 5/08; A01H 5/0812; A01H 5/02; A01H 5/00; A01H 6/88; A01H 6/78; A01H 6/00
See application file for complete search history.

(56) References Cited

U.S. PATENT DOCUMENTS

PP6,159 P 4/1988 Reisch
PP30,425 P3 4/2019 Clark

OTHER PUBLICATIONS

Coneva et al. Investigations to Determine the Performance of Recently Released Seedless Table Grapes and Advanced Selections from the University of Arkansas Breeding Program, Hort Science 48(9) (Supplement) 2013 SR—ASHS Annual Meeding Feb. 2-5, 2013, S33-S34. (Year: 2013).*
Double A Vineyards, Indulgence, retrieved on Jan. 26, 2022, retrieved from the Internet at https://doubleavineyards.com/indulgence, 2 pp. (Year: 2022).*
Clark J.R., et al. 2018. 'Opportunity' and 'Enchantment' wine grapes for the upper South of the United States. HortScience 53:1208-1211.
Double A Vinyards, Dazzle, retrieved on Jan. 25, 2022, retrieved from the Internet at https://doubleavineyards.com/dazzle, 2 pp. (Year: 2022).
Mayfield, S. Winemaking potential for new Arkansas wine grapes. Presentation. Horticulture Industries Show. Tulsa, OK. Jan. 10, 2020, 33 pp.
McWhirt, A.L. et al. 2021. Small Fruit Cultivar Recommendations for Arkansas. University of Arkansas System Division of Agriculture. FSA6130. https://www.uaex.edu/publications/PDF/FSA-6130.pdf, 8 pp.
Threlfall, R.T., et al. "'Indulgence' and 'Dazzle': Two New White Wine Grapes for the US Mid-South." HortScience 57.3 (2022): 453-457.
Threlfall, R.T., et al. 2019. Evaluating Winemaking Potential for University of Arkansas Wine Grape Cultivars and Selections. HortScience 54(9) (Supplement 2)—2019 SR-ASHS Annual Meeting. P. S382.
Threlfall, R.T. et al. 2020. Introduction to the Arkansas Quality Wine Program. Arkansas Association of Grape Growers Virtual Conference. Nov. 5, 2020. Schedule. 1 page.

* cited by examiner

*Primary Examiner* — June Hwu
(74) *Attorney, Agent, or Firm* — Quarles & Brady LLP

(57) ABSTRACT

Description and specifications of a new and distinct cultivar of wine grapevine which originated from a hand-pollinated cross of 'Seyval Blanc' (female parent) and 'Muscat Ottonel' (male parent) made in 1988. The seedlings fruited in the summer of 1992 in a vineyard near Clarksville, Ark. and one was selected for its potential as a wine grape for utilization in the Mid-South. The original vine was tested as 'Ark. 2359'. The new cultivar of grapevine is a white wine grape which is adapted to the Mid-South of the United States with good winter hardiness and distinct muscat flavor.

2 Drawing Sheets

Latin name: *Vitis* L. hybrid.
Varietal denomination: 'Indulgence'.

BACKGROUND

The new and distinct cultivar of grapevine named 'Indulgence' is described herein. The new cultivar originated from a hand-pollinated cross of 'Seyval Blanc' (not patented) and 'Muscat Ottonel' (not patented) made in 1988. The seedlings fruited in the summer of 1992 in a vineyard near Clarksville, Ark. and one was selected for its potential as a wine grape for utilization in the Mid-South of the United States. The original vine was tested as 'Ark. 2359'. The new cultivar of grapevine is a white wine grape which is adapted to the Mid-South of the United States with good winter hardiness and distinct muscat flavor.

SUMMARY OF THE INVENTION

The new and distinct cultivar of grapevine originated from a hand-pollinated cross of 'Seyval Blanc' (not patented) and 'Muscat Ottonel' (not patented) made in 1988 near Clarksville, Ark. The seeds resulting from this controlled hybridization were germinated in a greenhouse during the winter of 1988-89. Resulting seedlings were planted in the spring of 1989 in a vineyard near Clarksville, Ark. The seedlings fruited in the summer of 1992 and one seedling, designated Arkansas Selection 2359, was selected for its potential for processing and market production as a wine grape.

During late 1992 and early 1993, the original plant selection was propagated asexually at the above-noted location, by rooting hardwood cuttings. A test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the third season of growth in the vineyard after planting.

Vines of the new cultivar have good growth, not being excessively vigorous and good health as exhibited by good leaf color and no to minimal disease presence. It has produced well as own-rooted plants in all testing and has not been evaluated on any rootstocks. Adaptation to the Arkansas test site is very good as winter injury or heat damage were minimal.

The health of the new cultivar is good. Vines were evaluated for presence of the following diseases and were found to be moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), but were not tested for resistance to anthrancnose (*Elsinoë ampelina* Shear), and black rot (*Guignardia bidwellii* Viala & Ravaz). Fungal diseases can be fully controlled by the use of available fungicides.

Average harvest date of the new cultivar is 14 August in Clarksville, Ark. The berries are small (ave. 2.5 g) and globose in shape. Fruit is seeded. The flavor of the berry is fruity with strong muscat attribute and soluble solids average 16.5%. Fruit cracking and skin splitting has not been observed in severe rainfall pressure seasons. Clusters are medium in size, and well-filled. Average cluster weight is 153.1 g in Arkansas. Yield averages 16.6 kg/vine in Arkansas.

The flavor attributes for the new cultivar are reflective of commercial standards for quality juice and wine. Wine of the new cultivar is comparable to other muscat cultivars. Soluble solids and titratable acidity concentration of the juice at crush averages 16.9% and 0.64% respectively. Juice pH averages 3.29. The crush juice yield is 6.0 kg of grapes for 3.8 L of juice.

The new cultivar has been named 'Indulgence'.

BRIEF DESCRIPTION OF THE PHOTOGRAPHS

The accompanying photographs show typical specimens of the new cultivar in color as nearly true as it is reasonably possible to make in a color illustration of this character. The data collection was from vines that were 26 years old.

DETAILED DESCRIPTION OF THE NEW CULTIVAR

Figure 1:
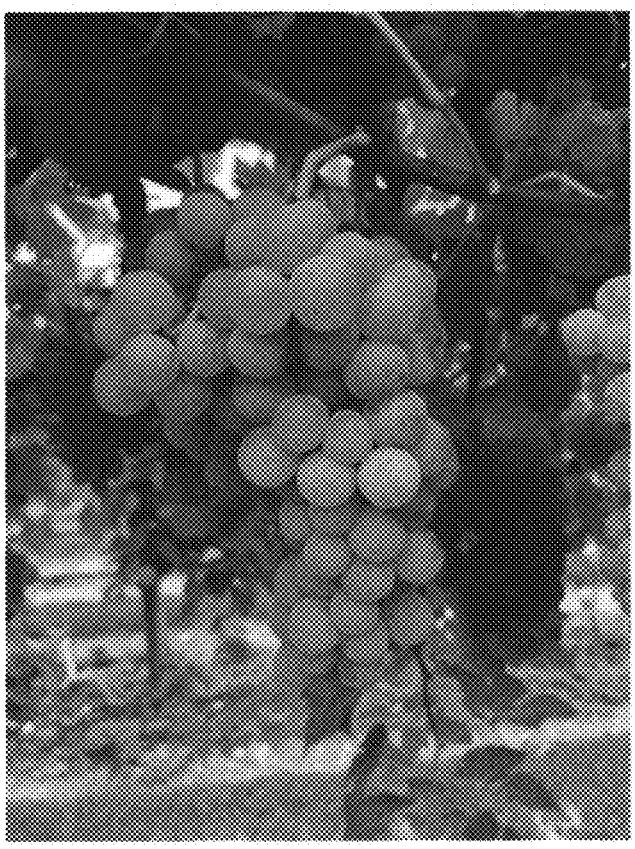
FIG. 1 is a photograph showing typical cluster of healthy fruit on the vine, near Clarksville, Ark.
Figure 2:
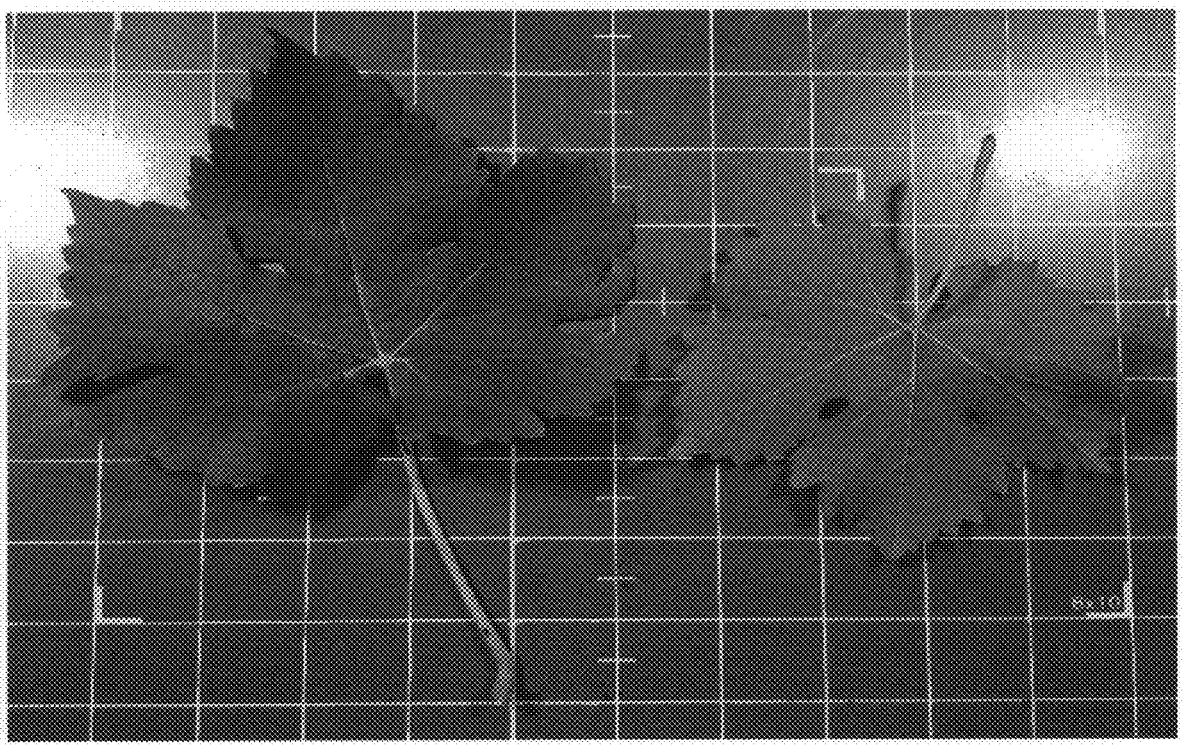
FIG. 2 is a photograph showing the leaf adaxial (left) and abaxial (right) view, near Clarksville, Ark.

'Indulgence' differs from its female parent 'Seyval Blanc' in that 'Indulgence' has strong muscat flavor whereas 'Seyval' is neutral in flavor. 'Indulgence' differs from its male parent, 'Muscat Ottonel', in that vigor is higher and cold hardiness is improved. Low temperatures have been observed to −15° F. without significant damage to the vine or crop load. 'Indulgence' is distinctly different from most other cultivated varieties of wine grapevines. 'Indulgence' carries a strong muscat flavor that holds present in young wines made from the grapes. This differs from 'Opportunity' (U.S. Plant Pat. No. 30,425), which carries a mild, neutral to fruity flavor. Soluble solid content of 'Indulgence' fruit averages 16.5%, in contrast to 'Opportunity', which has an average soluble solid content of 17.3%. 'Indulgence' has an average harvest date of 14 August, in contrast to 30 August for 'Opportunity'.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. Vines were fertilized annually in spring with Nitrogen or complete fertilizers. No shoot or leaf thinning practices were conducted on the vines.

Vine:

*Size.*—Evaluation vines are grown on a 1.5 m tall, single-wire trellis, bilateral cordon training system spaced 2.4 m between vines. Vines occupy this space fully.

*Growth vigor.*—Moderate, not excessive.

*Density of foliage.*—Light to moderate.

*Productivity.*—16.6 kg/vine.

*Rootstock.*—None; own-root.

*Cold hardiness.*—Hardy to −26° C. (−15° F.); potentially hardier as this was the coldest temperature experienced at the test site.

Shoots (current-season canes):

*Color of shoots (current-season canes).*—Sun exposed surface: yellow-green group 144C; shaded surface: yellow-green group 144C; no presence of anthocyanin on any portion of the current season shoots.

*Shoot attitude.*—Slightly upward.

*Openness of shoot tip.*—Slightly open.

*Prostrate hairs on young shoot tip.*—Dense.

Canes (mature, dormant):

*Color of mature, dormant cane.*—Base: greyed orange group 177B on shaded surface, greyed-orange group 177A on sun-exposed surface; midpoint: greyed-orange group 172D on shaded surface, greyed-orange group 172A on sun-exposed surface; terminal: greyed-orange group 160A on shaded surface, greyed-orange group 174B on sun-exposed surface; anthocyanin present on mature canes, greyed-orange group 174B.

*Texture of mature, dormant canes*.—Smooth.

*Shape of dormant cane*.—Round.

*Length of mature, dormant canes*.—73.0 cm.

*Diameter of mature, dormant cane*.—Base: 0.78 cm; midpoint: 0.54 cm; terminal: 0.33 cm.

*Internode length of mature, dormant canes*.—Base: 3.42 cm; midpoint: 5.79 cm; terminal: 3.31 cm.

*Lenticels*.—Present, but very few; size: 0.73 mm.

*Maturity in the fall*.—Canes were mature to tips in the fall.

Trunk:

*Diameter at 30 cm above soil level*.—3.47 cm.

*Shape*.—Angular.

*Trunk straps*.—Present.

*Surface texture*.—Rough, with peeling bark.

*Color*.—Inner bark color: greyed-orange group 165A; outer bark color: greyed-green group 195D.

Foliage:

*Arrangement of mature leaves*.—Simple and alternate.

*Shape of mature leaves*.—Lobed.

*Number of lobes on mature leaves*.—3 to 4 lobes.

*Petiole sinus of mature leaves*.—Wide open to slightly overlapped; depth: 3.48 cm; width: 1.0 cm.

*Venation of mature leaves*.—Arcuate.

*Teeth shape of mature leaves*.—Serrate, both sides straight to both sides convex.

*Size of teeth*.—Depth: 2.78 mm; width: 5.56 mm.

*Surface texture of mature leaves*.—Abaxial surface: smooth, no blistering; adaxial surface: smooth, no blistering.

*Dimensions of mature leaves*.—Length: 12.28 cm; width: 11.76 cm; thickness: 0.03 cm.

*Pubescence on mature leaves*.—Abaxial surface: none; adaxial surface: none; prostrate hairs between main veins: absent; amount of erect hairs on main veins: medium.

*Color of mature leaves*.—Base abaxial: yellow-green group 146B; base adaxial: green group 137C; midpoint abaxial: yellow-green group 146A; midpoint adaxial: green group 137A; terminal abaxial: yellow-green group 146B; terminal adaxial: green group 137A; no anthocyanin on any portion of mature leaves.

*Color of veins on mature leaves*.—Abaxial surface: yellow-green group 150B; adaxial surface: yellow-green group 145C; no anthocyanin on any portion leaf veins.

*Autumn coloration of mature leaves*.—Abaxial surface: yellow-orange group 19A; adaxial surface: yellow-orange group 22A.

*Leaf pubescence on young leaves*.—Abaxial surface: none; adaxial surface: none.

*Color of young leaves*.—Base abaxial: yellow-green group 145B; base adaxial: yellow-green group 145A; midpoint abaxial: yellow-green group 145B; midpoint adaxial: yellow-green group 145A; terminal abaxial: yellow-green group 145B; terminal adaxial: yellow-green group 145A; no anthocyanin present on any portion of young leaves.

*Vein color of young leaves*.—Abaxial surface: yellow-green group 145D; adaxial surface: yellow-green group 145D.

*Texture of young leaf veins*.—Abaxial surface: smooth; adaxial surface: smooth.

Petioles:

*Color of mature petioles*.—Yellow-green group 145B; sun-exposed areas are greyed-red group 180C.

*Anthocyanin present, mature petioles*.—Yes; color: red group 39C.

*Dimensions of mature petioles*.—Length: 6.81 cm; diameter: 2.15 mm.

*Color of young petioles*.—Yellow-green group 145A.

*Anthocyanin present, young petioles*.—Yes; color: red group 50C, primarily present on sun-exposed areas of petioles.

*Dimensions of young petioles*.—Length: 9.20 cm; diameter: 0.90 mm.

Tendrils:

*First tendril found at node number*.—6.

*Orientation*.—Alternate.

*Dimensions*.—Length: 11.75 cm diameter: 1.07 mm.

*Texture*.—Smooth, no pubescence present.

*Color of mature tendril*.—Yellow green group 146D.

*Shape and tendency*.—Tendrils are forked.

Buds:

*Number of buds on current, single-season cane*.—15.

*Dimensions of dormant buds*.—Width: 3.35 mm; length: 2.99 mm.

*Shape of dormant buds*.—Pyramidal to rounded pyramid (teardrop).

*Color of dormant buds*.—Greyed-orange group 174B.

*Texture of dormant buds*.—Smooth, no pubescence on scales; heavy pubescence on exposed tip of bud.

*Bud break*.—28 March, medium.

Disease resistance: Vines were evaluated for presence of the following diseases and found to be moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), but were not tested for resistance to anthrancnose (*Elsinoë ampelina* Shear), and black rot (*Guignardia bidwellii* Viala & Ravaz). Fungal diseases can be controlled by the use of available fungicides.

Flower:

*Fragrance*.—Mild, grassy.

*Sex*.—Hermaphrodite, perfect.

*Bloom dates*.—First bloom: 18 May; full bloom: 21 May; last bloom: 24 May.

*Flowers per cluster*.—260.

*Inflorescence dimensions*.—Length: 9.57 cm; diameter: 3.57 cm.

*Flower dimensions*.—Length: 5.29 mm; diameter: 3.40 mm.

*Flower longevity*.—<7 days, flowers mature and transition to fruit development quickly.

*Flower shape*.—Round; with calyptra, inconspicuous.

Stamens:

*Number*.—5.

*Color*.—Filament: yellow-green group 154D; anther: yellow-green group 153C.

Pistil:

*Number*.—1.

*Length*.—2.31 mm.

*Color*.—Yellow-green group 144A.

Pollen:

*Color*.—Yellow-green group 153C.

*Quantity*.—Moderate.

Petal:
*Number.*—6.
*Color.*—Yellow-green group 144A.
Sepals: Absent.
Pedicel:
*Dimensions.*—Length: 0.15 cm; diameter: 0.32 cm.
*Color.*—Yellow-green group 145A.
Fruit:
*Maturity.*—14 August.
*Berry shape.*—Globose.
*Berry shape in cross-section.*—Round/circular.
*Berry color.*—Skin: yellow-green group 146B, moderate waxy bloom present; flesh: yellow-green group 146C; anthocyanins: absent from flesh.
*Berry dimensions.*—Diameter at equator: 1.35 cm; diameter at base: 1.25 cm; diameter at apex: 0.85 cm; length: 1.45 cm.
*Berry weight.*—2.5 g.
*Berry skin texture.*—Smooth, slip skin.
*Firmness.*—Soft, 4.56 N of pressure required to compress the berry 5 mm. A Stable Micro Systems TA.XT.Plus Texture Analyzer (Texture Technologies Corporation, Hamilton, Mass.) was used. Fruit compression was performed by placing 5 individual berries on a flat surface using a cylindrical plane probe of 7.6 cm diameter at a rate of 2 $mm \cdot s^{-1}$ with a trigger force of 0.02 N. The probe traveled 5 mm after first contact, and the peak force (N) was recorded as berry firmness.
*Skin thickness.*—<1 mm.
*Tenacity.*—Moderate.
*Brush length.*—3.2 mm.
*Seeds.*—Present.
*Number of seeds per berry.*—2, fully developed.
*Seed size.*—Length: 6.68 mm; width: 3.43 mm; weight: 30 mg.
*Seed color.*—Greyed-orange group 166B.
*Juiciness.*—Moderate to high.
*Flavor.*—Fruity, with strong muscat attributes.
Juice:
*Soluble solids.*—16.5%.
*Titratable acidity.*—0.64 g/L tartaric acid.
*ph.*—3.23.
*Color.*—Yellow-green group 152D.
Cluster:
*Weight.*—153.1 g.
*Cluster dimensions.*—Length: 16.98 cm; width: 10.93 cm.
*Berries per cluster.*—103.
*Cluster per vine.*—220.
*Clusters per shoot.*—2.
*Peduncle (primary).*—Length: 6.15 cm; diameter: 1.02; color: yellow-green group 151D.
*Density.*—Moderately dense.
Use: Processing for white wine with improved vines particularly adapted for Arkansas and the Mid-South of the United States.

We claim:

1. A new and distinct cultivar of grape plant named 'Indulgence', substantially as illustrated and described.

* * * * *